United States Patent [19]

Welch

[11] Patent Number: 4,846,819

[45] Date of Patent: Jul. 11, 1989

[54] FEMALE INCONTINENCE DEVICE HAVING IMPROVED RIM STRUCTURE

[75] Inventor: Kathleen Welch, Milford, Conn.

[73] Assignee: Sherwood Medical Company, St. Louis, Mo.

[21] Appl. No.: 284,745

[22] Filed: Dec. 9, 1988

Related U.S. Application Data

[63] Continuation of Ser. No. 17,358, Feb. 24, 1987, abandoned.

[51] Int. Cl.$^4$ ............................................. A61F 5/44
[52] U.S. Cl. .................................. 604/329; 128/761; 604/336
[58] Field of Search .............. 604/317, 327–331, 604/336, 346–349, 355; 128/760, 761, 767; 4/144.1–144.4

[56] References Cited

U.S. PATENT DOCUMENTS

| | | |
|---|---|---|
| 3,528,423 | 9/1970 | Lee . |
| 3,646,929 | 3/1972 | Bonnar . |
| 3,661,155 | 5/1972 | Lindan . |
| 3,683,914 | 8/1972 | Crowley . |
| 3,705,575 | 12/1972 | Edwards . |
| 3,776,235 | 12/1973 | Ratcliffe et al. . |
| 3,800,800 | 4/1974 | Garbe et al. . |
| 3,995,329 | 12/1976 | Wiliams . |
| 4,019,498 | 4/1977 | Hawtrey et al. . |
| 4,139,006 | 2/1979 | Corey . |
| 4,194,508 | 3/1980 | Anderson . |
| 4,246,901 | 10/1981 | Bortle . |
| 4,280,498 | 7/1981 | Jensen . |
| 4,421,511 | 12/1983 | Steer et al. ............................ 4/144.3 |
| 4,455,691 | 6/1984 | Van Aken Redinger et al. .... 623/8 |
| 4,457,314 | 7/1984 | Knowles . |
| 4,496,355 | 1/1985 | Hall et al. . |
| 4,568,339 | 2/1986 | Steer ...................................... 604/329 |
| 4,578,065 | 3/1986 | Habib .................................... 604/336 |
| 4,621,029 | 11/1986 | Kawaguchi .......................... 428/447 |
| 4,690,677 | 9/1987 | Erb ........................................ 604/329 |

FOREIGN PATENT DOCUMENTS

| | | | |
|---|---|---|---|
| 2817571 | 10/1978 | Fed. Rep. of Germany ...... 604/329 |
| 2090144 | 7/1982 | United Kingdom ................ 604/239 |

OTHER PUBLICATIONS

"Misstique" Instruction Manuel (Corresponds to U.S. Pat. No. 4,496,355, (1985).

Primary Examiner—John D. Yasko
Assistant Examiner—Mario Costantino
Attorney, Agent, or Firm—Stanley N. Garber; Andrew J. Beck; Richard D. Allison

[57] ABSTRACT

An essentially leak proof urine collection device to be worn by a female which can be easily and comfortably positioned. The device is basically a receptacle, essentially semi-ovoid in shape, having an ovoid-shaped opening defined by a rim portion to which is attached an encapsulated deformable polymer gel ring which, when in use, substantially conforms itself to the contours of the vulvar tissue contacted by the gel, thus forming an essentially leak proof seal.

10 Claims, 1 Drawing Sheet

FEMALE INCONTINENCE DEVICE HAVING IMPROVED RIM STRUCTURE

This is a continuation of co-pending application Ser. No. 17,358 filed on Feb. 24, 1987 now abandoned.

BACKGROUND OF THE INVENTION

The present invention relates to an improve female urinary incontinence receptacle. More specifically the receptacle is formed with a polymer gel ring attached to the rim portion of the receptacle base. The gel ring which is made from a soluble silicon gel material provides a substantially leak-proof seal between the rim of the receptacle and the vulvar tissue of the user which it contacts.

Absorbent materials, e.g. pads and undergarments, and indwelling catheters are frequently used for treating urinary incontinence in females. Neither approach is suitable for extended periods of use or for females who while suffering from urinary incontinence otherwise lead normal active life styles, or who as a result of occupational circumstances cannot avail themselves of ordinary restroom facilities.

Absorbent pads are bulky, uncomfortable and non-hygienic. The pads must be changed frequently since urine trapped within is an excellent medium for the growth of microorganisms which can cause severe irritation and infection of sensitive skin which is in contact with the pad. Furthermore, there is also a significant risk of serious internal infection in absorbent pad users, particularly those who are bedridden.

Indwelling catheters likewise suffer from the disadvantage of causing irritation and internal infections. Moreover, catheterization is unsuitable for generally active females.

A preferred approach to female urinary incontinency involves the use of a cup-like receptacle which is designed so as to surround substantially the urogenital region and collect urinary discharge. Such receptacles are generally formed with an opening in the bottom to which is connected a drainage tube for transporting the urine to a suitable urine collection means, for example a bag secured to the leg of the user. The receptacles may vary in size with larger models externally surrounding the entire urogenital area, whereas smaller receptacles fit internally within the urogenital area, i.e., between the labia major, thereby surrounding essentially the urethral opening. The larger style of receptacle is generally held in place by means of a vaginal insert member affixed to the receptacle and a supporting garment. Smaller receptacles, which can be used internally, may be held in place by the labia major alone, an attached vaginal insert member, an adhesive, and/or a support garment.

Urine leakage, however, is a major problem with both the larger and smaller types of receptacles. The major reason for this problem is an inability of these devices to effect an essentially leak-resistant seal between the rim of the receptacle and the vulvar tissue which it contacts.

The rim portion of known female incontinence devices is generally smooth. Such smooth rim portions mate poorly with the irregular surface contours of the urogenital region and thus the devices are prone to urine leakage. Several attempts have been made to remedy this problem. For example, it has been taught in U.S. Pat. No. 4,198,979 to coat the smooth rim surface of the receptacle with a suitable adhesive which will bond the rim to the vulvar tissue. It has also been taught in the prior art to fabricate the receptacle from materials such as polymethacrylates which become pliant at body temperature and pressures to conform to the configuration of the vulvar tissues. See e.g. U.S. Pat. No. 4,270,539. However, it has been found that ethylpolymethacrylate, for example, hardens and loses its shape over time. It is also known that polymethacrylates can vary in shrinkage and resiliency by varying the polymer composition.

In fact, none of the devices disclosed in the prior art have provided an optimum seal so that urine leakage, along with associated irritation and infection, have continued to be major problems.

These problems are substantially eliminated by the present invention which provides for a urine receptacle having a deformable polymer gel attached to the rim portion which conforms to the vulvar contours to make an essentially leak-resistant seal.

SUMMARY OF THE INVENTION

Accordingly, it is a principal object of the present invention to provide an essentially leak-proof urine collection device to be worn by a female. The device of the invention is a receptacle, essentially semi-ovoid in shape, having an ovoid-shaped opening defined by a rim portion to which is attached an encapsulated deformable polymer gel ring which, when in use, substantially conforms itself to the contours of the vulvar tissue which the gel contacts, thus forming a leak-proof seal.

In accordance with the invention, the polymer gel ring is prepared from a cured cross-linked silicone gel which is encapsulated within a flexible encapsulant formed from a silicone elastomer, both of which conform to the contours of the vulvar tissue, while, at the same time, the encapsulating material prevents the polymer gel from bleeding.

Apart from the foregoing object of providing an essentially leak-proof urine receptacle, it is a further object of the present invention to provide a urine collection device which does not utilize a vaginal insertion member, but is easily and comfortably positioned in regard to the anterior wall of the vaginal opening, thus permitting simultaneous use of tampons during menstruation. Accordingly, the device has a generally ventral/dorsal orientation when worn in a standing position with the dorsal end being tapered and curved upwardly to conform to the natural arch of the vulvar anatomy between the urethral orifice and anterior surface of the vaginal opening.

Other objects, features and advantages of the present invention will be apparent by reference to the following description of preferred embodiments, drawings and claims.

BRIEF DESCRIPTION OF THE DRAWINGS

The invention may be better understood from the following detailed description, taken in conjunction with the accompanying drawings in which.

DESCRIPTION OF THE PREFERRED EMBODIMENTS

Figure 1:
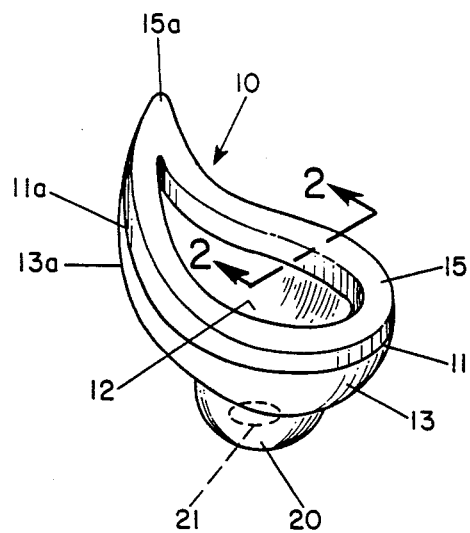
FIG. 1 is a perspective view of the urine collection device.

In accordance with a preferred embodiment of the present invention, the urine collection device 10 shown in FIG. 1 is a generally semi-ovoid cup-like structure molded of a rigid thermosetting material such as silicone. Device 10 which may be fabricated in a variety of standard sizes to surround inter alia the entire urogenital opening has an essentially flat surfaced rim portion 11 on an upper surface and substantially rigid, generally concave, wall surface 13 integrally connected thereto, the rim 11 and wall surfaces 13 together defining an ovoid shaped opening 12 which surrounds, inter alia, the urethral opening. Attached to the top planar surface of rim portion 11 is a deformable polymer gel ring 15 fabricated of a gel material which, in texture and firmness, matches as closely as possible, and can contour itself to mate substantially with, the irregular surface of vulvar tissue of the recipient with which it is in contact, thus forming a comfortable, essentially leak-free seal.

Figure 2:
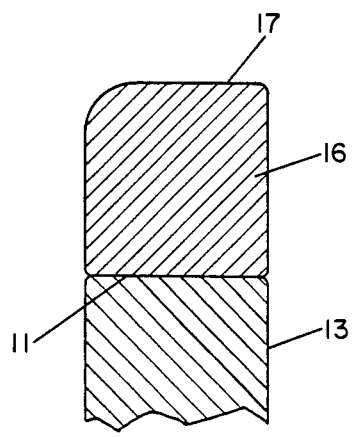
FIG. 2 is a cross-section through line 2—2 of FIG. 1.

With reference to FIG. 2 which is a cross-section through polymer gel ring 15, it is seen that the polymer gel ring 15 has a basically two part configuration in that an internal polymer gel structure 16 formed, for example, from silicone gel is encapsulated within a flexible encapsulant layer 17, formed e.g., from a silicone elastomer.

Figure 3:
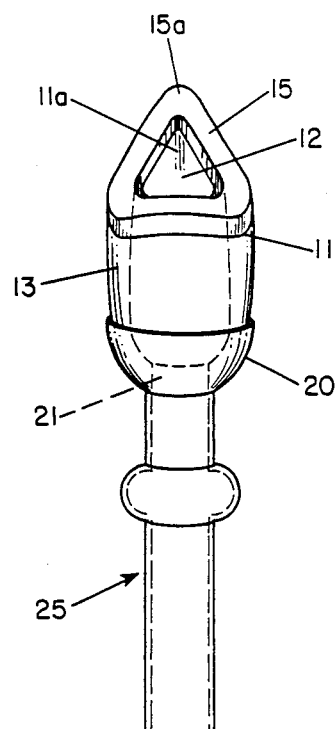
FIG. 3 is a front view of the urine collection device of FIG. 1 together with a conduit means.
Figure 4:
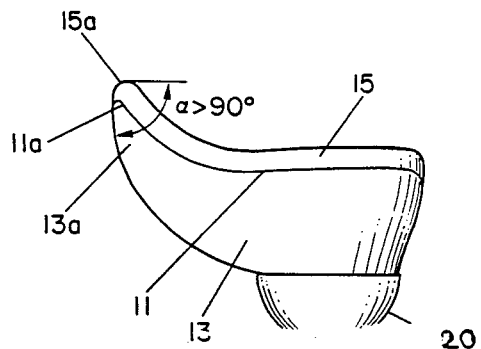
FIG. 4 is a side view of the urine collection device.

When worn by a female in the standing position, the device is oriented in a generally ventral-dorsal direction. As seen in FIGS. 3 and 4, the dorsal end of device 10 including the rim 11a, gel ring 15a, and wall portions 13a is tapered, substantially vaginally non-invasive and curved upwardly at an angle slightly greater than 90 degrees (see reference angle of FIG. 4) in order to conform substantially to the natural arch of the vulvar anatomy between the urethral orifice and the anterior surface of the entrance to the vaginal opening.

The urine collection device 10 is formed with a semi-spherical, generally concave protuberance 20 (FIG. 1) located on the exterior bottom portion of wall surface 13. An opening 21 is formed in the bottom of said protuberance which is in communication with the opening 12 of the device. A conduit or tube member 25 (FIG. 3) is adhesively adhered to the exterior bottom portion 20 so as to communicate with opening 21 formed therein, thereby providing means for transporting the urine from the receptacle to a collection device, such as a bag, which can be strapped to the user's leg.

EXAMPLE

The following procedure is preferred for preparing the urine collection device 10. It is to be recognized that the present invention encompasses other methods known to those skilled in the art which fall within the scope and spirit of the invention.

The base of the receptacle, i.e., rim portion 11, wall portion 13, and protuberance 20, was cast from a prepared dentstone and plastic mold combination. The dentstone and plastic molds were prepared by (1) casting a thermoform plastic mold from a brass mold by means of vacuum thermoforming equipment; (2) pouring dentstone into said prepared plastic mold and allowing the dentstone to solidify therein; and (3) drilling said solidified dentstone into the desired shape, preferably by means of a Dremel tool, such that when the dentstone mold was inserted into the plastic mold, a space, preferably equidistant in all directions was formed between the opposing wall surfaces of the dentstone mold and the plastic mold.

To form the base of the receptacle, a suitable thermosetting plastic polymer, e.g., a silicone elastomer, was first poured into the plastic mold and then the dentstone mold was inserted therein. After the polymer had set, the dentstone mold was removed, thus resulting in a base having the general rim and wall structures of device 10. A preferred silicone, for the base was silicone elastomer MDX-4-4210, mixed with 360 Medical Fluid, obtained from Dow Corning Medical Products, Inc. and prepared according to the manufacturer's instructions. The elastomer, curing agent and medical fluid were combined in such ratios as to provide a finished cured product having Durometer (Shore A Hardness) of approximately 30. For example, it has been found that a silicone elastomer prepared according to the manufacturer's instructions in the following combination was suitable for use in preparing the base of the device:

Dow Corning ® MDX-4-4210 Clean Grade Elastomer

Dow Corning ® 360 Medical Fluid (1 part)

Dow Corning ® MDX-4-4210 Clean Grade Elastomer

Curing Agent (1 part)

After mixing in the appropriate ratios, the silicone elastomer was de-aerated, poured into the prepared mold and allowed to cure at 70 degrees C. for three hours before removing the dentstone mold.

The deformable polymer gel ring was then cast and cured directly on top of the base. After the dentstone mold was removed, a dentstone insert was placed into the center of the cured silicone base so that the base would remain hollow during the subsequent steps. The polymer gel is preferably a silicone polymer gel, although urethane prepolymers which, upon mixing with water, form a gel can also be used. The gel should be chosen to match as closely as possible, in respect to texture and firmness, the urogenital tissue, such that a soft, comfortable, essentially leakproof seal is formed. A particularly preferred gel, prepared generally according to instructions was the silicone gel PEG015 of Petrarch Systems, Inc. This gel was formed from a two-component system designated A and B which can be mixed in a variety of ratios to obtain a desired firmness and texture. For the instant device the gel was mixed in a 7:1 A/B (silicone elastomer/curing agent) ratio such that the penetration level of the gel was at least 200 mm. The gel was mixed, de-aerated, poured directly onto the prepared cured silicone base, and allowed to cure at 70 degrees C. for one hour.

Suitable polyurethane foam gels with optimal physical properties for use in place of silicone gels in the present device include the Aquapol gels from the Freeman Chemical Corporation.

Since silicone gels are known to bleed, it is preferable to enclose them within an encapsulant to prevent bleeding. After the gel had cured, the dentstone centerpiece insert was removed. An encapsulant, e.g., a barrier elastomer, was then applied in a thin layer to the gel to prevent bleeding of the gel. A preferred encapsulating material was the flexible encapsulant OE produced by Petrarch Systems, Inc., which is a two component solventless silicone elastomer with a vinyl addition cure type. The OE encapsulant was mixed in a 10:1 ratio, as described by the manufacturer, deaerated, coated onto the silicone polymer gel and cured at 70 degrees C. for 10 minutes.

A second encapsulant, which provided a tough shell or barrier for the gel was then applied. A preferred encapsulant for this purpose was PELD 15 from Petrarch Systems, Inc. which is described by the manufacturer as a silicone elastomer with maximum pliability and non-gel properties. PELD 15 is also a two component system: A=base, B=vinyl addition/curing agent. The elastomer as used in the device should have a Durometer (Shore A Hardness) no greater than 14 with a tear strength (Die B Tear) no less than 30 pli. The PELD 15 elastomer encapsulant was mixed according to manufacturer's instructions at a ratio of 1.25:1 A/B, deaerated, coated onto the polymer gel, and cured for one hour at 70 degrees C.

A final coating of the OE encapsulant, prepared and applied as described above, was then added to the encapsulated gel ring to rid the finished product of any tackiness.

The foregoing device, processing steps and techniques are merely illustrative of those currently preferred. Many modifications of said device, processing steps and techniques will be obvious to those skilled in the art and hence, what is specifically disclosed is not intended in any way to limit the scope of the invention claimed hereinbelow.

I claim:

1. A urine collection device to be worn by a female comprising a receptacle having a top opening surrounded by a rim defined by integrally formed side and bottom wall surfaces wherein the top opening is sufficiently large to surround the urethral opening of the female without contacting or invading the urethral opening, a deformable gel ring attached to said rim wherein said gel ring consists of an encapsulant layer which substantially encloses a gel layer therein and wherein said gel ring contours itself to mate substantially with the surface contours of the vulvar tissue of the female wearing the device.

2. The device according to claim 1 wherein the receptacle is semi-ovoid in shape and wherein said rim and wall portions define an opening sufficiently large enough to surround and enclose the urethral opening and portions of the vulvar tissue of the female wherein the device has ventrally and dorsally oriented ends when worn by a female in a standing position.

3. The device according to claim 2 wherein the dorsally oriented end of said device is tapered and curves upwardly to conform to the natural arch of the vulvar anatomay between the urethral opening and the anterior surface of the vaginal opening.

4. Device according to claim 2 in which the dorsal end is tapered and curved upwardly to conform to the natural arch of the vulvar anatomy between the urethral opening and the anterior surface of the vaginal opening in such a way that the dorsal end is substantially vaginally non-invasive.

5. The device according to claim 1 wherein the encapsulant layer is a cured silicone elastomer having more flexibility than the rim and wall surfaces of the device and wherein the encapsulant layer entirely encloses the gel layer of the gel ring.

6. The device according to claim 1 wherein the rim and wall surfaces are formed from a high strength, stable cured silicone rubber elastomer having less flexibility than the gel ring of said device.

7. The device according to claim 1 wherein the gel layer is a cured cross-linked silicone gel entirely enclosed by said encapsulant layer.

8. Device according to claim 1 in which the flexible encapsulant is a cured silicone elastomer.

9. The device according to claim 1 further comprising a bottom opening formed in the bottom wall of said receptacle and includes a conduit means communicating therewith.

10. A urine collection device to be worn by a female comprising a receptacle having top and bottom openings wherein said top opening is surrounded by a rim defined by integrally formed side and bottom wall surfaces wherein the top opening is sufficiently large to surround and enclose the urethral opening of the female without contact or invasion of the urethral opening by the device, a deformable gel ring attached to said rim wherein said gel ring consists of a flexible encapsulant layer enclosing an inner gel layer and wherein said gel ring contours itself to mate substantially with the surface contours of the vulvar tissue of the female wearing the device and wherein the device includes ventral and dorsal ends wherein the dorsal end of said device is tapered and curves upwardly to conform substantially to the natural arch of the vulvar anatomy between the urethral orifice and the anterior surface of the vaginal opening.

* * * * *